(12) United States Patent
Frick

(10) Patent No.: US 7,433,041 B2
(45) Date of Patent: Oct. 7, 2008

(54) ILLUMINATION ARRANGEMENT FOR A COLOUR MEASUREMENT DEVICE

(75) Inventor: Beat Frick, Buchs (CH)

(73) Assignee: X-Rite Europe AG, Regensdorf (CH)

( * ) Notice: Subject to any disclaimer, the term of this patent is extended or adjusted under 35 U.S.C. 154(b) by 204 days.

(21) Appl. No.: 11/353,536

(22) Filed: Feb. 14, 2006

(65) Prior Publication Data

US 2006/0192963 A1      Aug. 31, 2006

(30) Foreign Application Priority Data

Feb. 16, 2005    (CH) .................................... 0264/05
Feb. 28, 2005    (CH) .................................... 0340/05

(51) Int. Cl.
*G01N 21/25*     (2006.01)
(52) U.S. Cl. ..................................... 356/416
(58) Field of Classification Search ................ 356/319, 356/420, 416; 362/227, 231, 216
See application file for complete search history.

(56) References Cited

U.S. PATENT DOCUMENTS 6,809,347 B2 * 10/2004 Tasch et al. ................. 257/103

2005/0052648 A1    3/2005 Frick et al.
2005/0117334 A1 *  6/2005 Lee et al. .................... 362/231
2005/0135079 A1 *  6/2005 Yin Chua et al. ............ 362/231

FOREIGN PATENT DOCUMENTS

EP            1507134            2/2005

* cited by examiner

*Primary Examiner*—Kara E Geisel
(74) *Attorney, Agent, or Firm*—McCarter & English, LLP

(57) ABSTRACT

An illumination arrangement for a color measurement device includes a linear arrangement of light emitting diode chips (11) packed tightly along a narrowly defined path. A plurality of light emitting diode chips within at least one region of the path emit light of substantially the same color and are directly covered together with a resin in which a converter material is included for the conversion of the light emitted by the light emitting diode chips of the plurality thereof into at least one other wavelength range. An illumination light with cosine characteristic is emitted from a surface of the resin. UV light emitting regions and non-UV light emitting regions as well as regions including color filters and/or polarization filters may be provided. The illumination arrangement may include white emitting regions and narrow band emitting regions constructed especially for color density measurement.

20 Claims, 3 Drawing Sheets

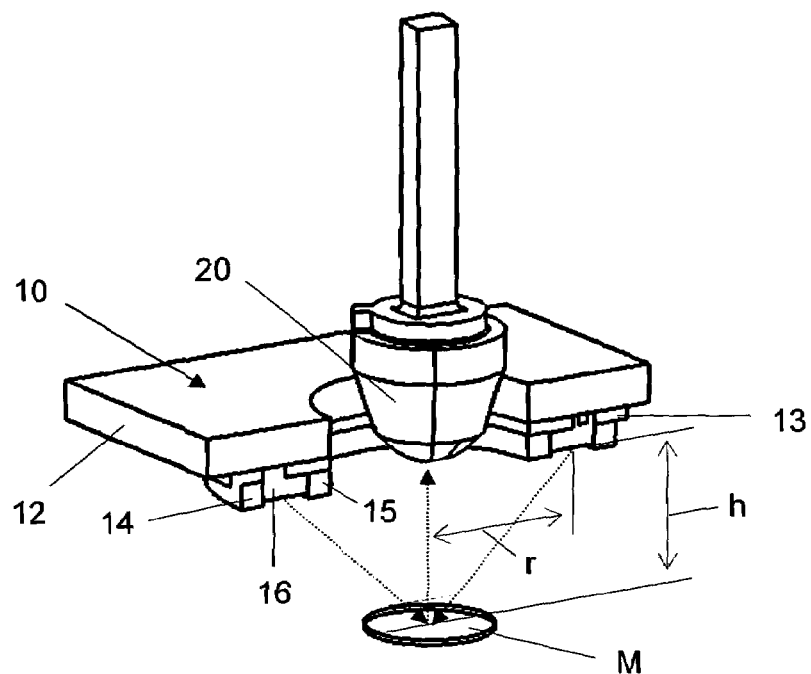
Fig. 1
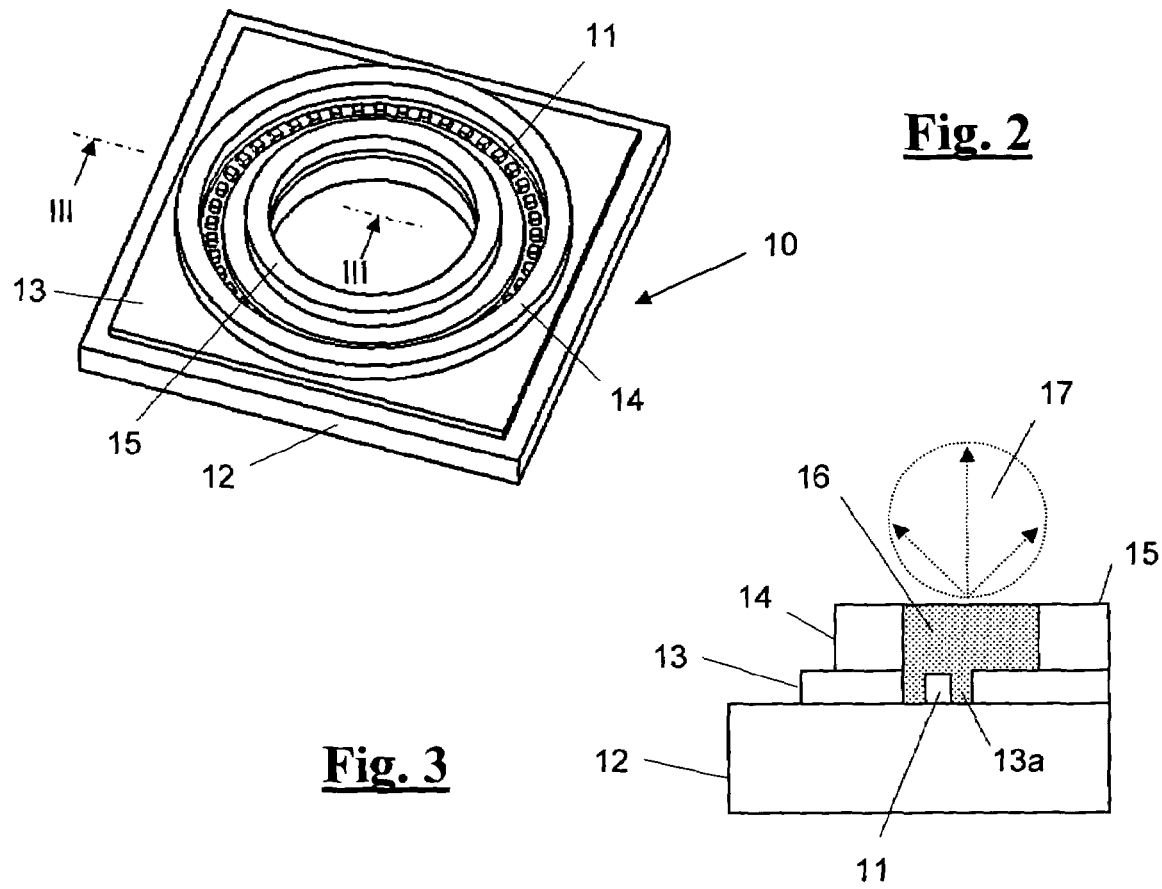
Fig. 2
Fig. 3

ILLUMINATION ARRANGEMENT FOR A COLOUR MEASUREMENT DEVICE

The invention relates to an illumination arrangement for a colour measurement device. In particular, the present invention deals with an illumination arrangement for use in point-by-point or line-by-line scanning spectrophotometers.

The mentioned requirements and limitations also place increased demands on the illumination arrangement of the measurement device.

An illumination arrangement of the generic type is now to be improved by the present invention with respect to its performance, precision, relative simplicity of manufacture and universality of use.

This object underlying the invention is achieved by an illumination arrangement for a colour measurement device, especially a point-by-point or line-by-line measuring spectrophotometer with several light sources in the form of light emitting diodes constructed as consign emitters, which is constructed as a linear array of light emitting diodes, whereby many individual light emitting diode chips are closely packed along a small, narrowly defined straight, partially straight or curved, especially circular line and at least partially cast in resin in which at least regionally a converter material for the conversion of the light emitted from the light emitting diodes into other wavelength ranges is included.

Preferred embodiments and further developments of the illumination arrangement in accordance with the invention are the subject of the dependent claims.

Figure 4:
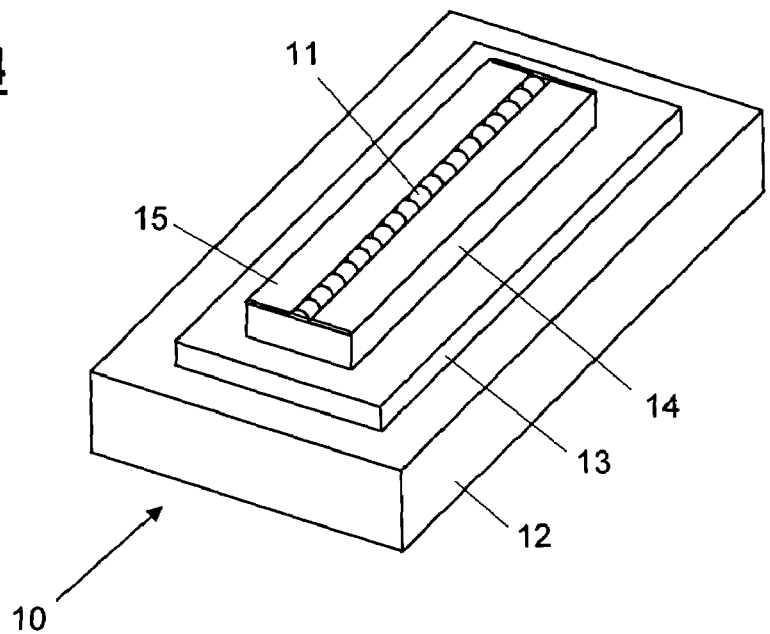
Figure 5:
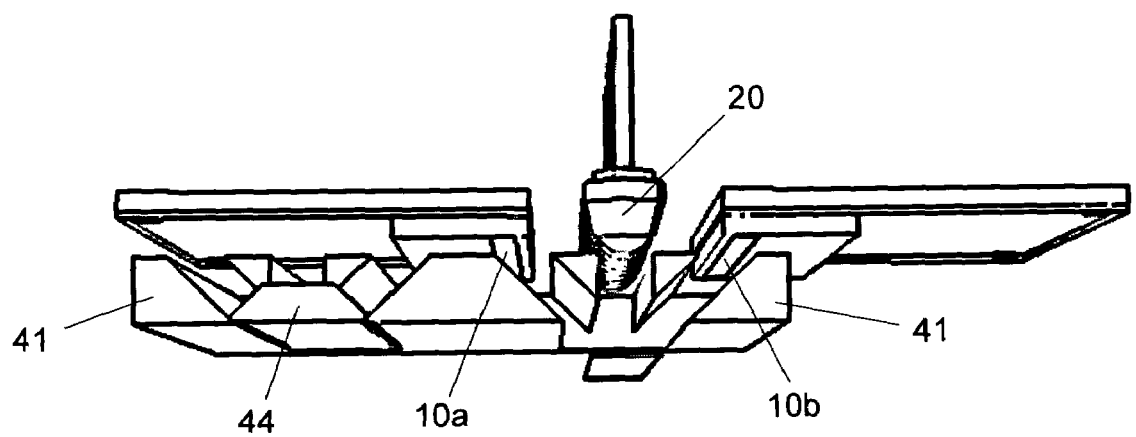
Figure 6:
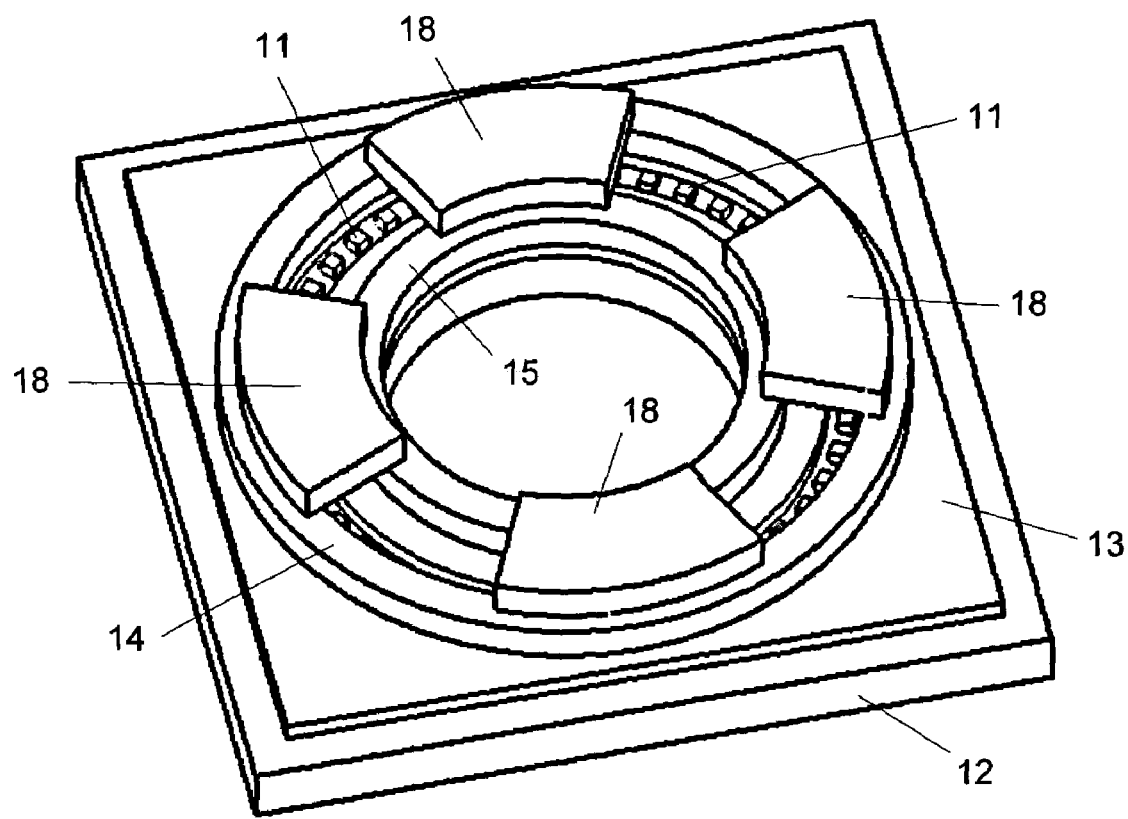

The invention is further described in the following by way of the drawings. It shows:

FIG. 1 a partially sectional view of a first exemplary embodiment of the illumination arrangement in accordance with the invention in connection with the pickup head of a spectrophotometer;

FIG. 2 a bottom view of the illumination arrangement of FIG. 1;

FIG. 3 a cross-section along line 3-3 in FIG. 2;

FIG. 4 a bottom view of a second exemplary embodiment of the illumination arrangement in accordance with the invention;

FIG. 5 a partial view of a line-by-line scanning device with two illumination arrangements according to FIG. 4; and FIG. 6 a bottom view of a preferred further development of the illumination arrangement of FIG. 2.

The illumination arrangement illustrated in FIG. 1 is constructed as an annular illumination device and as such is especially suited for use in colour measurement devices scanning individual measurement points, especially spectrophotometers. The figure shows the measurement light pickup head 20 of a spectrophotometer described, for example, in the U.S. patent application Ser. No. 10/894,797, around which the illumination arrangement is coaxially positioned. The contents of this U.S. application are incorporated herein by reference.

As is apparent especially also from FIGS. 2 and 3, the illumination arrangement which as a whole is referred to by reference number 10 includes a large number of individual light emitting diode chips 11, which are densely packed in a small and narrowly defined circular ring, which coaxially surrounds the optical axis of the pickup head 20. The typical size of the individual light emitting diode chips is about $0.4*0.4*0.4$ mm$^3$. The plane of the light emitting diode ring is in the practical use perpendicular to the optical axis of the pickup head 20 and is thereby oriented parallel to the measurement plane M.

The mechanical construction of the illumination arrangement 10 which is in this example ring-shaped is apparent from the cross-sectional illustration in FIG. 3. A circuit board 13 is positioned on a base plate 12 which is a good heat conductor and two coaxial annular walls 14 and 15 are positioned on the circuit board. An annular groove 13a is cut into the circuit board. The light emitting diode chips 11 are positioned in the groove 13a and directly adhered onto the base plate ("die bonding"). The electrical contacts of the light emitting diode chips are connected by way of not illustrated fine wires with corresponding contact surfaces on the circuit board 13 ("wire bonding"), which provides the connection to a here not illustrated external electronic control, whereby also a selective control of the individual light emitting diodes 11 and/or of groups of light emitting diodes 11 can be provided. The space between the two annular walls 14 and 15 is filled with a resin which includes a converter material (illuminant) for the conversion of certain wavelength ranges of the light emitted by the light emitting diodes into other wavelength ranges. This will be described in more detail further below. The illumination light is emitted from the surface of the cast resin 16 with consign characteristic (Lambert emitter), which is indicated in FIG. 3 by arrow 17. The main direction of emission (radiation) is thereby perpendicular to the plane of the light emitting diode ring.

The use of light emitting diodes (LED) as light sources for the illumination has many advantages. LEDs have a long service life and can be switched on and off quickly and in a very short time, whereby they are correspondingly energy efficient. By cycling the illumination and by differentiating between a measurement with the LEDs "on" and a following measurement with the LEDs "off" one can eliminate the auxiliary light influence during the measurement. LEDs do not emit heat radiation (IR) to the illuminated region. LEDs are available in specific spectral ranges, for example white, UV, R, G, B, etc. Typical commercially available light emitting diode products are Lumiled Emitter, Osram Golden Dragon, Cree Xlamp, etc.

In the circular illumination arrangement of FIG. 2, blue LED chips (at about 450 nm) and/or UV-LEDs (at about 390 nm) are used and together covered with a resin with converter (illuminant). A high light density is achieved by the dense population and small, narrowly defined line form.

The concept in accordance with the invention of the narrowly populated LED-line and the common casting of the LEDs with a converter containing resin is of course not limited to circular illumination arrangements. For example, a straight linear illumination arrangement can also be constructed according to the same principle, as it is required, for example, in line-by-line scanning devices. FIG. 4 shows an exemplary embodiment of the illumination arrangement in accordance with the invention constructed as such a straight line shaped illumination. The construction is analogous to the circular illumination so that no further explanation is required.

Depending on the intended use, it can also be advantageous to position the light emitting diodes along a partially straight or otherwise curved line.

Relevant parts of an example of a line-by-line scanning device are illustrated in FIG. 5, whereby the longitudinal direction of the scanning devices extends essentially perpendicular to the drawing plane. One recognizes linear, sequentially positioned pickup heads 20 analogous to the one in FIG. 1, two straight linear illumination arrangements 10a and 10b and a brightness reference arrangement with a movable sled 41 and positioned thereon a longitudinal, in cross-section trapezoid redirecting arrangement 44 in measurement position, which means outside the illumination and scanning beam path. When it is in the beam path, the redirecting arrangement 44 serves as brightness reference and redirects the light originating from the illumination arrangements 10a and 10b onto the pickup heads 20. The redirecting arrangement 44 is not relevant for the present invention.

The illumination concept in accordance with the invention with densely packed light emitting diode lines (straight or annular arrangement) enables the optimal adaptation of the illumination to specific application conditions. The illumination arrangement can be manufactured simply and cost efficiently with narrow tolerances.

For measurement technology reasons, an annular illumination is optimal for use in a point-by-point scanning spectrophotometer, since the preselected establish illumination geometry standards are best accomplished thereby while the highest light flow in the measurement spot is achieved at the same time. For line-by-line measurement apparatus, a line-shaped illumination with two symmetrically positioned illumination lines is optimal.

In the linear or circular LED lines of the illumination arrangement 10 and according to a further preferred aspect of the invention, different LED types (R, G, B, UV) can be positioned in regions (line portions or annular segments) and/or cast respectively with resin with different converter types, or possibly also completely without converter. For example, a region with individually switchable UV-LEDs without converter produces pure UV light for the controlled excitation and measurement of brighteners in the paper. A region with individually switchable R, G, B-LEDs without converter produces light in a narrow spectral range and is used for a controlled density measurement. (When one illuminates only in a narrow spectral region, the residual scattered light in the spectrometer is highly reduced.). Regions with switchable blue or UV-LEDs and cast with specific R, G, B converters also produce light in a narrow spectral range, which can be used for the controlled density measurement.

In the linear or circular LED lines, different regions (line sections or annular segments) can be covered with different filters such as polarization, R, G, B or UV filters as is illustrated in FIG. 6 by way of the example of the annular illumination. The filters are therein labeled with numeral 18. The illustrated four time symmetry is thereby preferred for reasons of measurement technology.

For example, a region with individually switchable LEDs which are covered by a polarization filter emits polarized light, another region with individually switchable LEDs without polarization filter emits unpolarized light. The switching from polarized to unpolarized light can thereby be carried out purely electrically by corresponding switching on and off of the respective LEDs, obviating complex mechanical switching. For this application, a crossed polarization filter must be rigidly integrated as analyzer in the pickup channel, which however is not of hindrance during unpolarized measurement.

Another region with switchable white LEDs which is covered with an R, G or B filter emits in a narrow spectral range and again serves for the improvement of the density measurement.

A further individually switchable region with UV filter allows, when very broadband white LEDs (with emission from 380 nm UV to 730 nm deep red) are used, an electrical on and off switching of the UV portion by control of the corresponding region.

The control of the LEDs in the individual regions of the illumination arrangement is carried out, as already mentioned, by way of an electronic control which possibly receives corresponding commands from a superior internal or external control.

Light emitting diodes suited for measurement technology use and converter material suitable therefor are described in the technical literature and the data sheets of the pertinent manufacturers (for example Lumiled). An encompassing overview of the associated prior art was provided in a lecture "illuminants for white LEDs in the general illumination" by Dr. Stefan Tews (Litec LLL GmbH, Greifswald, Germany) as part of a VDI-conference in 2004.

White LEDs are used for the invention with YAG-illuminants or preferably ortho-silicate illuminants (BOSE) as converter (illuminant). These illuminants can be manufactured in different colors and can also be mixed, while the absorption and emission are spectrally separated. The illuminants can be pumped from blue (about 450 nm) to UV (about 390 nm).

According to page 25 of the lecture, the combination of a blue LED (452 nm) with two BOSE-LS-converters (blue-green, 508 nm and deep orange, 595 nm) provides a massive improvement compared to YAG. It is thereby important that the minimum between the LED emission maximum at about 450 nm and the converter emission above 500 nm is avoided as much as possible.

The "best" combination of a UV-LED with a mixture of various converters is illustrated on page 26 of the lecture. The spectrum is thereby well covered from 400 nm to 700 nm and the colour reproduction (colour rendering index) is excellent. The LED emits at 392 nm, and the converter types BAM (blue, 450 nm), BOSE (green, 515 nm), BOSE (orange, 593 nm) and silicate-germanate-LS (red, 657 nm) are used.

This LED converter combination is especially advantageous, since a UV LED is thereby used which can also be used as UV source for the specific excitation of paper brighteners.

In numerous applications of a colour measurement device or spectrophotometer, for example for the measurement of a printed sheet, the scanning must be contact free. The contact surface of the sheet over a relatively large area of the sheet is generally not perfectly even. Therefore, distance variations occur during scanning. They cannot influence the measurement results. This requires that the illumination arrangement 10 and the pickup head 20 must be distance independent over the tolerated range of a few tenths of millimeters.

The visual field of the pickup head is illuminated by the illumination arrangement. Since the angle of capture of the pickup head is very limited (according to the colour measurement standards only angles of capture of +/−5° are tolerable) the illumination or beam density in the measurement field is measured, which is independent from the distance. Therefore, the illumination arrangement only needs to produce a constant illumination strength which is independent from the distance.

A suitable solution for a distance independent illumination under 45° is described in the above already mentioned EP-A 1 507 134 (corresponding to U.S. patent application Ser. No. 10/894,797 of Jul. 20, 2004). A radiation source with a Lambert emission characteristic is thereby positioned parallel to the plane of the measurement field. The position of the radiation source relative to the measurement field is selected such that the light hits the measurement field at an angle of 45°. According to the basic photometric law, a distance insensitivity is thereby achieved over a range of distance variations which is sufficiently large for the practice.

The annular illumination arrangement according to the invention is constructed and positioned according to exactly the same principals. The distance independence is achieved when the plane of the light emitting diode ring is parallel to the measurement plane and a distance a of the ring from the measurement plane is selected to be equal with the radius r of the ring (FIG. 1). When the illumination arrangement is constructed as a linear light emitting diode line, the distance independence is fulfilled with sufficient approximation when the distance of the light emitting diode line from the optical axes of the pickup heads is the same as the distance to the measurement plane.

The invention claimed is:

1. An illumination arrangement for a color measurement device, the illumination arrangement comprising:
    a linear arrangement of light emitting diode chips packed tightly along a narrowly defined path;
    wherein within at least one region of the narrowly defined path, the linear arrangement comprises a plurality of light emitting diode chips emitting light of substantially the same color and directly covered together with a resin in which a converter material is included for the conversion of the light emitted from the light emitting diode chips of the plurality thereof into at least one other wavelength range; and
    wherein an illumination light with cosine characteristic is emitted from a surface of the resin.

2. The illumination arrangement according to claim 1, wherein the linear arrangement of light emitting diode chips includes light emitting diode chips with respectively different spectral characteristics.

3. The illumination arrangement according to claim 1, wherein within at least one region of the narrowly defined path, the linear arrangement emits UV light, and within at least another region of the narrowly defined path, the linear arrangement emits non-UV light, whereby the UV light emitted in the at least one region is suited for the excitation of brighteners in paper.

4. The illumination arrangement according to claim 1, wherein within at least one region of the narrowly defined path, the linear arrangement includes color filters.

5. The illumination arrangement according to claim 1, wherein within at least one region of the narrowly defined path, the linear arrangement includes polarization filters.

6. The illumination arrangement according to claim 1, wherein within at least one region of the narrowly defined path, the linear arrangement emits white light, and within at least another region of the narrowly defined path, the linear arrangement emits narrow band light.

7. The illumination arrangement according to claim 6, wherein the at least another region of the narrowly defined path that emits narrow band light is constructed for color density measurements.

8. The illumination arrangement according to claim 1, wherein within at least one region of the narrowly defined path, the linear arrangement includes narrow band converter materials.

9. The illumination arrangement according to claim 1, wherein the converter material includes ortho-silicate illuminants (BOSE).

10. The illumination arrangement according to claim 1, wherein the light emitting diode chips of the linear arrangement are selectively controllable.

11. The illumination arrangement according to claim 10, wherein the light emitting diode chips of the linear arrangement are selectively controllable individually or in groups.

12. The illumination arrangement according to claim 1, wherein the color measurement device is a point-by-point or line-by-line measuring spectrophotometer.

13. The illumination arrangement according to claim 1, wherein the narrowly defined path is at least one of straight, partially straight, curved or circular.

14. The illumination arrangement according to claim 1, wherein the linear arrangement of light emitting diode chips is ring-shaped, and wherein a main direction of emission associated with the illumination light is substantially perpendicular to a plane defined by the ring-shaped linear arrangement.

15. The illumination arrangement according to claim 1, wherein the illumination arrangement includes a base plate and a circuit board positioned on the base plate, wherein a groove is defined in the circuit board that exposes a surface of the base plate, the light emitting diode chips of the linear arrangement are positioned in the groove and mounted with respect to the base plate, and at least a portion of the resin is cast into the groove in the circuit board.

16. The illumination arrangement according to claim 15, wherein the light emitting diode chips of the linear arrangement are directly adhered onto the base plate.

17. The illumination arrangement according to claim 16, wherein the light emitting diode chips of the linear arrangement are adhered onto the base plate via a die bonding technique.

18. The illumination arrangement according to claim 15, wherein the electrical contacts of the light emitting diode chips of the linear arrangement are connected to corresponding contact surfaces of the circuit board via fine wires.

19. The illumination arrangement according to claim 18, wherein the electrical contacts of the light emitting diode chips of the linear arrangement are connected to the corresponding contact surfaces of the circuit board via a wire bonding technique.

20. The illumination arrangement according to claim 14, wherein the illumination arrangement includes a base plate and inner and outer annular walls mounted with respect to the base plate, wherein a space is defined between the inner and outer annular walls that exposes a surface of the base plate, the light emitting diode chips of the linear arrangement are positioned in the space and mounted with respect to the base plate, and at least a portion of the resin is cast into the space between the inner and outer annular walls.

* * * * *